(12) United States Patent
Deleye et al.

(10) Patent No.: US 9,835,450 B2
(45) Date of Patent: Dec. 5, 2017

(54) METHOD FOR INSPECTING AN OBJECT BY MEANS OF ULTRASOUND

(75) Inventors: Xavier Georges Jose Deleye, Rotterdam (NL); Andries Gisolf, Delft (NL); Adrianus Maria Cornelius Van Den Biggelaar, Lekkerkerk (NL)

(73) Assignee: RONTGEN TECHNISCHE DIENST B.V., Rotterdam (NL)

( * ) Notice: Subject to any disclaimer, the term of this patent is extended or adjusted under 35 U.S.C. 154(b) by 633 days.

(21) Appl. No.: 13/641,734

(22) PCT Filed: May 3, 2010

(86) PCT No.: PCT/NL2010/050258

§ 371 (c)(1),
(2), (4) Date: Oct. 17, 2012

(87) PCT Pub. No.: WO2011/139142

PCT Pub. Date: Nov. 10, 2011

(65) Prior Publication Data

US 2013/0041597 A1    Feb. 14, 2013

(51) Int. Cl.
*G06F 19/00*    (2011.01)
*G01B 17/02*    (2006.01)
(Continued)

(52) U.S. Cl.
CPC ......... *G01B 17/02* (2013.01); *G01N 29/043* (2013.01); *G01N 29/069* (2013.01); *G01N 29/11* (2013.01)

(58) Field of Classification Search
CPC .......... G01N 29/069; G01N 2291/044; G01N 2291/02854; G01N 29/07; G01N 2291/103; G01N 29/11; G01B 1/00; G01S 15/8993

(Continued)

(56) References Cited

U.S. PATENT DOCUMENTS 4,497,210 A * 2/1985 Uchida et al. .................. 73/602
4,606,015 A * 8/1986 Yamaguchi ..................... 367/95
(Continued)

OTHER PUBLICATIONS

Examination Report dated Feb. 19, 2014 issued to the corresponding Australian patent application.
(Continued)

*Primary Examiner* — Toan Le
*Assistant Examiner* — Jeffrey Aiello
(74) *Attorney, Agent, or Firm* — Jacobson Holman, PLLC.

(57) ABSTRACT

A method for inspecting an object by ultrasound for detecting a wall thickness or defects of the object, wherein at least one ultrasonic pulse is transmitted into the object on a first position on an object's surface, the ultrasonic pulse is received on a second position on an object's surface possibly by propagating directly towards the second position along the surface or possibly as a result of reflection and/or diffractions of the pulse so that more than one pulse being received at different time and wherein a data signal is generated representing the received pulses and the associated moments in time wherein these pulses are received wherein the step is repeated for other positions and wherein the data signals are processed for generating processed signals to obtain a To FD image, wherein the processing for obtaining the processed data signals comprises at least three processing steps.

18 Claims, 10 Drawing Sheets

(51) Int. Cl.
*G01N 29/04* (2006.01)
*G01N 29/06* (2006.01)
*G01N 29/11* (2006.01)

(58) Field of Classification Search
USPC ........... 73/597, 627, 601; 367/87, 99; 702/1, 702/39, 128, 159
See application file for complete search history.

(56) References Cited

U.S. PATENT DOCUMENTS

| | | | | |
|---|---|---|---|---|
| 5,119,678 | A * | 6/1992 | Bashyam et al. ................ | 73/602 |
| 6,092,420 | A * | 7/2000 | Kimura et al. ................. | 73/620 |
| 6,105,431 | A * | 8/2000 | Duffill et al. .................... | 73/624 |
| 6,128,092 | A * | 10/2000 | Levesque et al. ............. | 356/451 |
| 8,210,045 | B2 * | 7/2012 | Caron ................ | G01N 29/2418 73/597 |
| 2007/0169554 | A1 * | 7/2007 | Bestebreurtje .................. | 73/614 |
| 2007/0277611 | A1 * | 12/2007 | Portzgen ................ | G01N 29/07 73/592 |
| 2009/0007678 | A1 * | 1/2009 | Fukutomi et al. .............. | 73/598 |
| 2010/0307249 | A1 * | 12/2010 | Lesage et al. .................. | 73/623 |
| 2012/0226159 | A1 * | 9/2012 | Sinclair ............... | G01S 7/52046 600/443 |
| 2013/0041597 | A1 * | 2/2013 | Deleye ................... | G01B 17/02 702/39 |

OTHER PUBLICATIONS

F.H. Dijkstra et al., "Time of Flight Diffraction and Acceptance Criteria: A Perfect Team," Materials Evaluation, Mar. 1998, pp. 395-398.

M. Nishio, "Examination of structures by a new non-destructive examination technique," Welding International, Aug. 1, 2008, vol. 22, No. 8, pp. 504-510.

L. Wei et al., "Sparse deconvolution method for improving the time-resolution of ultrasonic NDE signals," NDT and E International, Jul. 2009, vol. 42, pp. 430-434.

R. Demirli et al., "Model-Based Estimation of Ultrasonic Echoes Part II: Nondestructive Evaluation Applications," IEEE Transactions on Ultrasonics, Ferroelectrics, and Frequency Control, May 2001, vol. 48, No. 3, pp. 803-811.

* cited by examiner

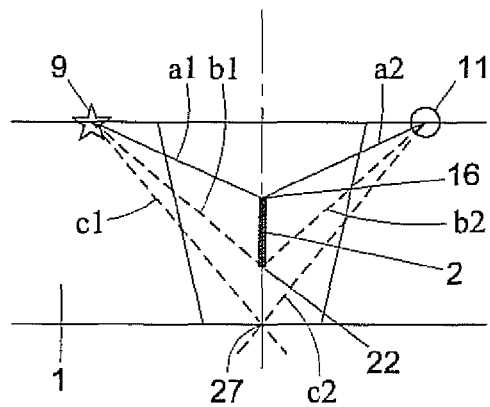
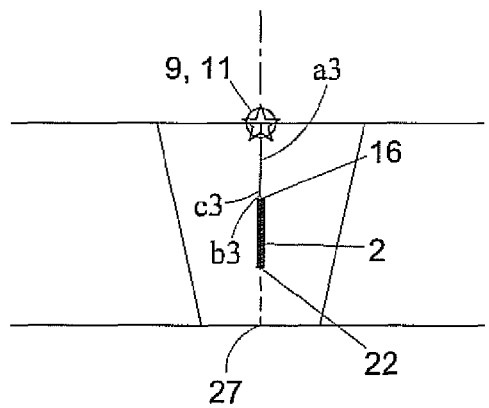
Fig. 4a
Fig. 4b
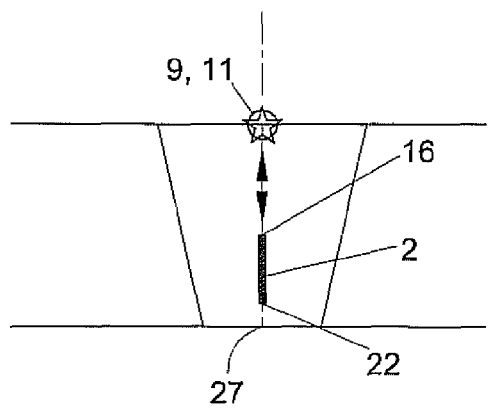
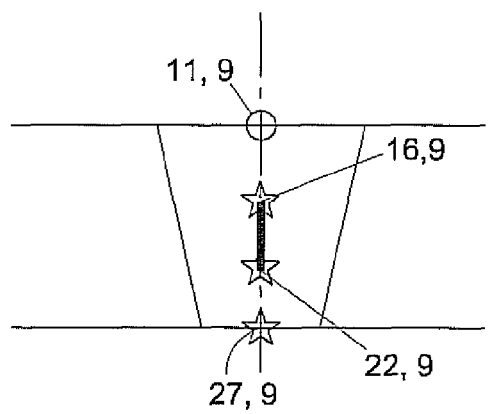
Fig. 4c
Fig. 4d ature affects signal phase (diffractions from upper and lower boundaries of an imperfection have opposite phases). The resulting ToFD image is always a combination of the actual defect characteristics and the ultrasonic behavior intrinsic for a ToFD examination. The operator is trained in dealing with these aspects, and has software tools at his/her disposal to support interpretation (hyperbolic cursors, lateral wave removal, lateral wave straightening, contrast enhancement etc.).

METHOD FOR INSPECTING AN OBJECT BY MEANS OF ULTRASOUND

This is a national stage of PCT/NL10/050258 filed May 3, 2010 and published in English, hereby incorporated by reference.

The present invention relates to a method for inspecting an object by means of ultrasound, for example for detecting a wall thickness of the object or for detecting defects in the object, wherein in a step a. at least one ultrasonic pulse is transmitted into the object on a first position of a surface of the object, the ultrasonic pulse is received on a second position of the surface of the object possibly by propagating directly towards the second position along the surface of the object or possibly as a result of reflection and/or diffractions of the pulse in the object so that the transmitted pulse may result in more than one pulse being received at different moments in time and wherein a data signal is generated representing the received pulses and the associated moments in time wherein these pulses are received wherein step a. is repeated for other first positions and/or second positions for generating a first set of data signals and wherein the first set of data signals obtained in the plurality of steps a. are processed for generating processed signals on the basis of which a ToFD image can be obtained.

The principle of the Time of Flight Diffraction (ToFD) technique is well known. Developed in the UK in the seventies ToFD is now a widely accepted Non-Destructive Testing (NDT) technique, both in new construction and In Service NDT. Various studies have been conducted to evaluate its performance in terms of detection and sizing capabilities. European standards for its use as well as acceptance levels for indications found with ToFD have been developed and several national schemes for qualification of ToFD operators are in place.

Similar to radiography, the interpretation of ToFD images is mainly based on the ability of the operator to recognize typical patterns. Similar to other NDT techniques, operators need a certain level of training in order to be able to reliably detect and accurately size defects. Although signal amplitude, together with noise level, is important for the visibility of relevant signals in the ToFD image, it is not directly used as a parameter for defect detection and characterization. Recognition of signal phase however is relevant for the operator to maximize sizing accuracy. The way how signals appear in a ToFD image is strongly influenced by factors such as ultrasonic frequency, resolution, beam spread (causing typical hyperbolic tails to the indication) and the presence of noise (random noise and material scatter). Defect Although trained operators are able to do this, interpretation may be time consuming and affected by the human factor. Because of this, it could have significant advantages to process ToFD data in such a way that intrinsic effects are automatically removed by the software, making interpretation much more straightforward and, as a further step, introduce the possibility of automatic interpretation.

In the past, several attempts were taken towards automated interpretation of ToFD images. Such approaches were usually based on algorithms mimicking interpretation by an operator and were partly based on the use of neural networks. Although such algorithms exist, automated interpretation remained difficult because relevant signals are not always clearly visible between noise and small insignificant artifacts, such as gas pores.

An application where a simple image processing for automated interpretation could work is detection and quantification of root corrosion and erosion with ToFD. FIG. 1a shows a typical ToFD image obtained in such an exercise. Using the ToFD image (bitmap) as a basis, the contour of the backwall echo A (marked black in the figure) is automatically detected and its time of flight at any point along the weld compared to the time of flight of the lateral wave B (white line in the figure). This allows for an accurate display of the remaining wall thickness C as a function of position along the weld, see FIG. 1b wherein the wall thickness C is shown and arrows D show maximum and minimum wall thickness.

However, such an approach will only work if no disturbing factors are present in the image, such as indications of weld imperfections. Such factors would disturb the evaluation. Smoothing can help, but only to a certain extent. To deal with these limitations, the invention described is not using image processing, but data processing. The idea is to apply data processing first, making interpretation of an image obtained on the basis of the processed data easier and more straightforward, and then consider automated interpretation of the improved image.

In view of the above, according to the invention, the method is characterized by the characterising portion of claim 1.

Thus, according to the invention, at least processing step b. and/or processing step c. and/or step d. are used for obtaining the process signals on the basis of which an improved ToFD image can be obtained.

Step b. is a step which improves the recognition of defects in the ToFD image. The first substep and second substep of step b. are necessary for being able to carry out the third substep of step b. This third stub step collapses the diffraction curves of the pores (defects with no length in the scanning direction) if on the basis of the data signals which are processed by the third substep a ToFD image would be obtained (in the usual manner). The scanning direction is the direction of displacement of lines between successively used first and second positions for transmitting and receiving pulses. Most often the distance between the first and second position is fixed and the lines are parallel to each other). As a result of this processing step (third substep), in such ToFD image the defects with lengths in the scanning direction still have a shape even after processing, but now show that true lengths and shapes, whereby the effect of beam spread has been removed. Defects with no length in the scanning direction do not anymore have a hyperbolic shape but show a dot which in fact also indicates the true length of such indication. Thus the resolution in the scanning direction is improved by carrying out step b.

In case the data signals which are obtained in step b. are used for subsequently carrying out said step c. the result is that if based on the data signals provided in step c. a ToFD image is obtained, said ToFD image is even more easy to use for interpretation. This is caused by the fact that disturbing influences (pulse length, hyperbolic shape, noise, interference) have been significantly reduced or even removed. Also reflections of the wall as well as a received lateral wave, can be found as lines with an improved sharpness within such ToFD image. Thus in the ToFD image the resolution in the time direction is improved.

In case one is only interested in determining a wall thickness, it is also possible to carry out step c. as such. In that case, the processing for obtaining the process signals does not comprise step b. but does comprise step c. It is also possible to carry out step d. as such, both for measuring defect and determining a wall thickness. If step d. is also applied, the resolution of a ToFD image in the time direction (distance to the surface) can be further improved. Step d. can also be applied in combination with step b. and/or step c.

According to a preferred embodiment, it holds that step b. further comprises a fourth substep wherein each data signal of the third set of data signals is processed in the fourth substep wherein the fourth substep is the inverse of the first substep so that the third set of data signals is transformed back to signals representing the true first position and the true second position. The ToFD image which is used nowadays has the characteristics that its time axis is not linear with respect to a distance between a position within the object and the surface of the object.

The reason that step b comprises at least the first substep, the second substep and the third substep is as follows. The first substep corrects the data signals such that if on the basis of such corrected date signals, a ToFD image would be obtained, the time axis of the image is linear with a distance between a position within the object and the surface of the object. Therefore this first substep is also called a normal move out correction step. Preferably the first substep comprises also correcting the data signal such that the corrected data signal simulates a pulse, which is received as a result of the transmitted pulse propagating as a lateral wave from the first position to the second position, to be received on the same moment in time whereon the pulse is transmitted. This is because the first position and the second position coincide so that the time for a pulse to travel along the surface of the object from the first location to the second location would be zero.

Furthermore the propagation velocity of the pulse within the body used for the imaging of data should be assumed half of what the real propagation velocity is. This is simulated by carrying out the second substep. The object of the second substep is thus to process the data signals in such a way that the individual data signals together simulate a single physical measurement, where all secondary sources (i.e. reflectors and diffractors) in the body fire (reflect or diffract the pulse) from the actual position within the body simultaneously at a predetermined time (for example at the predetermined time (t=t0).

Preferably it holds that the second set of data signals which are generated by carrying out the first substep and the second substep also simulate that a pulse, which is received as a result of the transmitted pulse propagating as a lateral wave from the first position to the second position, will be received on the same moment in time whereon the pulse is transmitted (primary source) and which is also the same moment in time whereon the secondary sources fire (fire means the actual reflecting or diffracting a transmitted pulse within the body). This can be realized in two ways.

According to the first way the first substep comprises also correcting the data signal such that the corrected data signal simulates a pulse, which is received as a result of the transmitted pulse propagating as a lateral wave from the first position to the second position, to be received on the same moment in time whereon the pulse is transmitted. If subsequently in the second substep is carried out wherein it is simulated that the lateral wave propagates with half the velocity of what the real propagation velocity is, the result remains the same for the lateral wave, namely that the pulse which is received on the basis of the lateral wave is received on the same moment in time whereon the pulse is transmitted. (distance to travel from the first position to the second position is equal to zero). Thus the primary source and the secondary sources are simulated to fire simultaneously at a predetermined time (for example at t=to) wherein the secondary sources fire on the actual positions where the pulse is diffracted or reflected.

According to the second way the second step in addition comprises correcting a data signal for the propagation velocity of the ultrasound propagating along the surface of the object from the first position to the second position which correction simulates a measurement wherein this propagation velocity along the surface is infinite. The result will again be that an pulse which travels along the surface of the object from the first position to the second position will be received on the same moment in time whereon it was transmitted. Thus the primary source and the secondary sources are simulated also to fire simultaneously wherein the secondary sources fire on the actual positions where the pulse is diffracted or reflected and wherein the primary source fires at the position where the first position and second position are corrected to coincide.

If this condition is met, it is possible to apply the third substep on the signals obtained by means of the second substep. The data signals obtained by the second substep are referred to as the second set of data signals.

The third substep comprises inverse wave field extrapolation on the resulting second set of data signals. The second set of data signals is back propagated to every point in the image space, through a medium with half the real rate propagation speed and only the zero time sample of the back propagated wave fields is retained. If in an image point a secondary source fires at time equals zero, an image amplitude will be obtained in this way. If no secondary source was present, the resulting image amplitude will be zero. On the basis of such corrected data signals an improved ToFD image can be obtained as indicated above.

If however, based on the data signals which are obtained by the third substep, a ToFD image would be obtained, the ToFD image would have a vertical axis which is linear with a distance between a position within the body and the surface of the body. This is of course a very good image which can be used for interpretation, however, many operators are still used to work with non-lineair ToFD images. Therefore, by means of the fourth substep the data signals which are obtained by means of the third substep are corrected in such a way that a ToFD image is obtained with the usual non-lineair vertical axis.

If step d. is also applied, the resolution of a ToFD image in the time direction (distance to the surface) can be further improved. It is noted that step d. should be applied before step c. if step c. is applied. Thus if the data signals are processed in several steps, including steps d. and c., step d. is carried out before step c. is carried out. If step d. is carried out before step c., step d. may be carried out before step b., after step b., or between any of the substeps of step b. If step c. is not carried out, step d. may be carried out before step b., after step b., or between any of the substeps of step b. Step d. may also be carried out without being combined with step b. and or step c. In that case determining a wall thickness can be carried out more accurately then in the prior art methods.

According to a preferred embodiment of the invention the processing of the first set of data signals comprises the step d. wherein in step d. in each data signal the phase of the transmitted pulse is removed wherein this phase comprises the phase spectrum in combination with the amplitude spectrum of the transmitted pulse.

According to a preferred embodiment the ToFD image obtained based on the processed data signals according to the invention is automatically evaluated to determine defects in a wall and/or thickness of the wall.

The invention will now be further discussed, based on some examples in the drawing, wherein:

FIG. 1b shows a wall thickness obtained by the ToFD image of FIG. 1a;

FIG. 2b shows the system of FIG. 2a in a direction of the arrow P in FIG. 2a;

FIG. 2c shows a data signal obtained by the system according to FIG. 2a;

FIG. 3a shows a ToFD image based on a first set of data signals directly obtained by the system according to FIG. 2a;

Figure 3A:
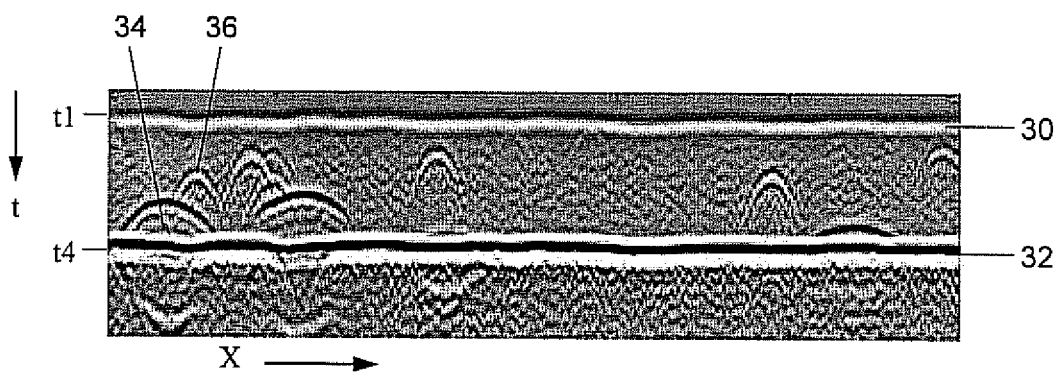
Figure 3B:
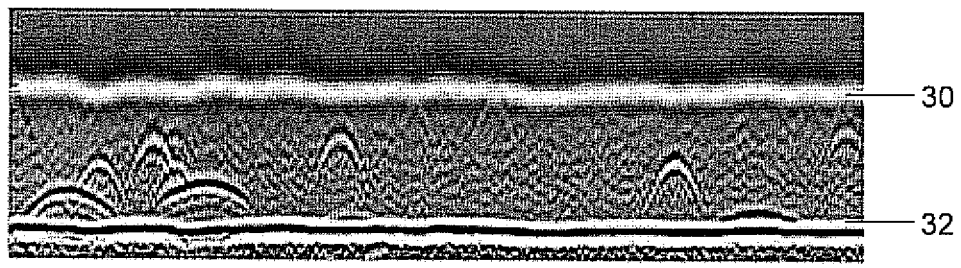
FIG. 3b shows a ToFD image based on the set of data signals used for obtaining the ToFD image according to FIG. 3a after being processed according to a first substep incorporating a normal move out correction.
Figure 3C:
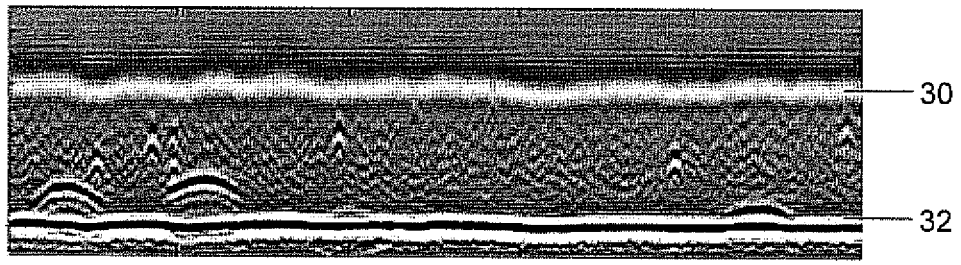
Figure 3D:
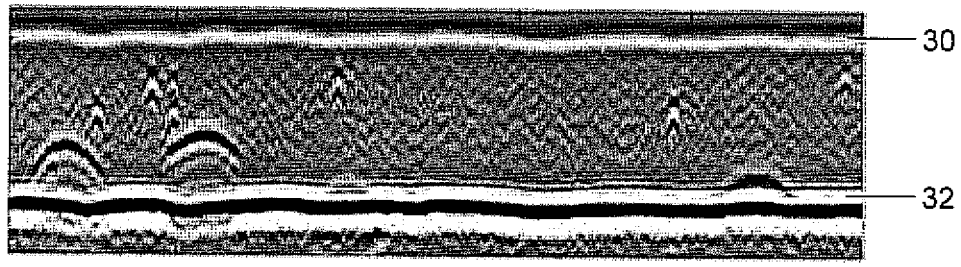
Figure 3E:
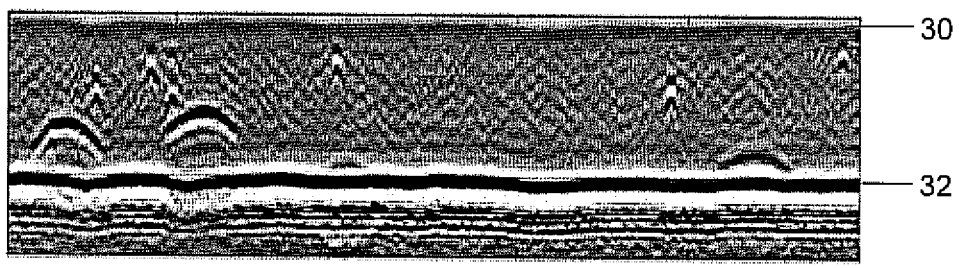
Figure 3F:
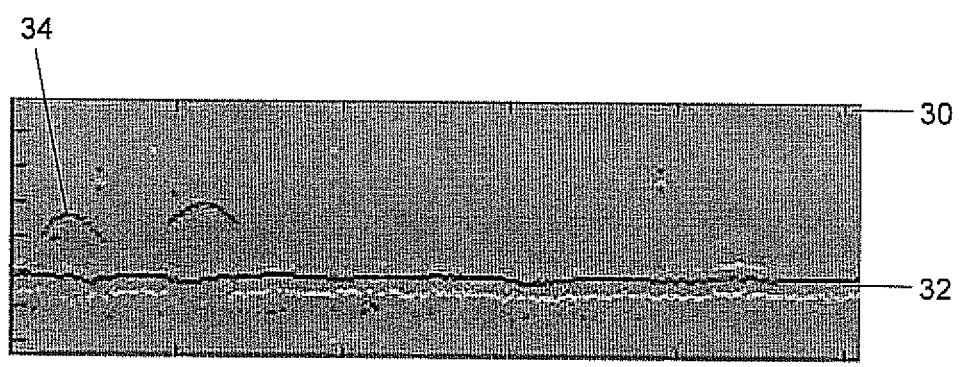
Figure 5A:
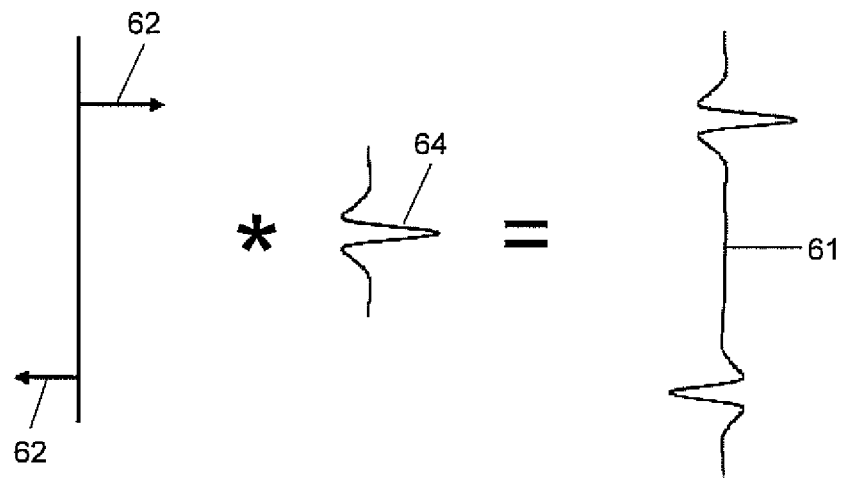
Figure 5B:
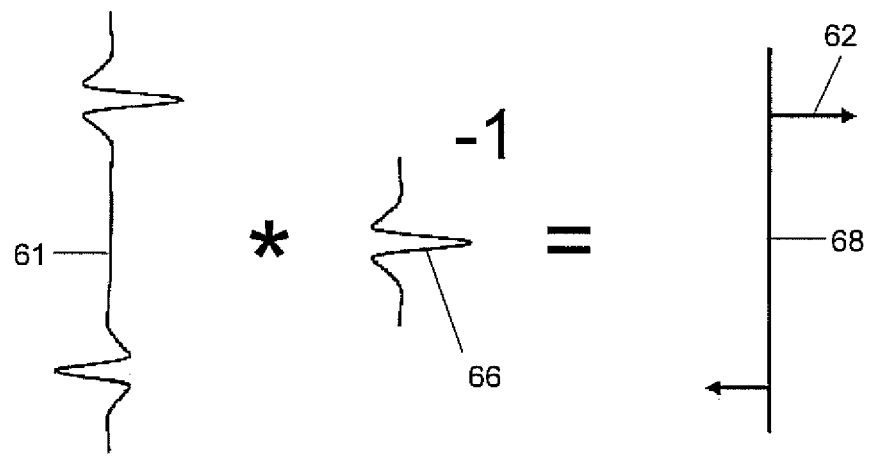
Figure 6:
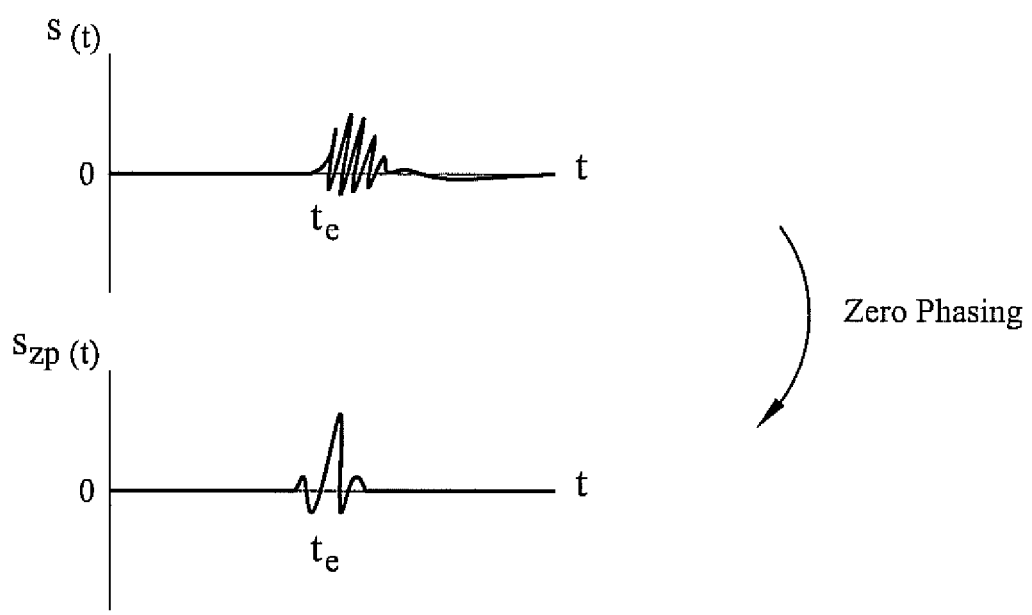
Figure 7:
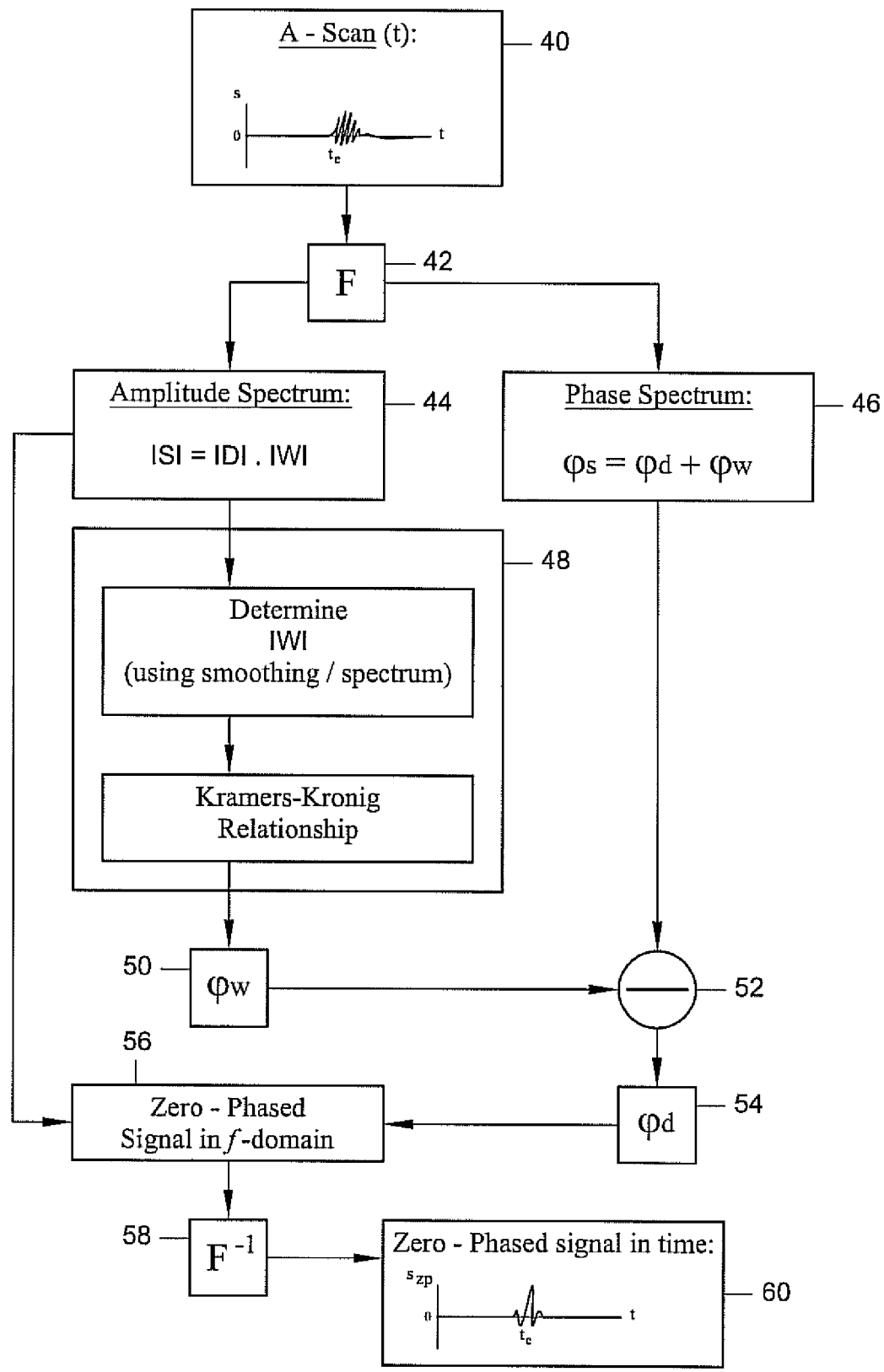
Figure 8A:
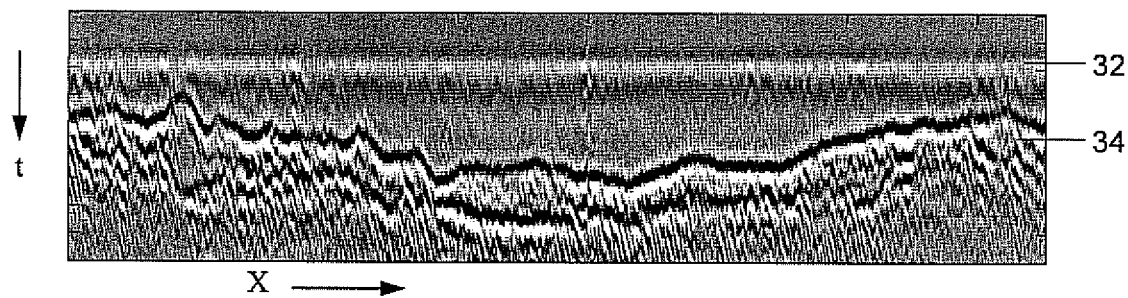
Figure 8B:
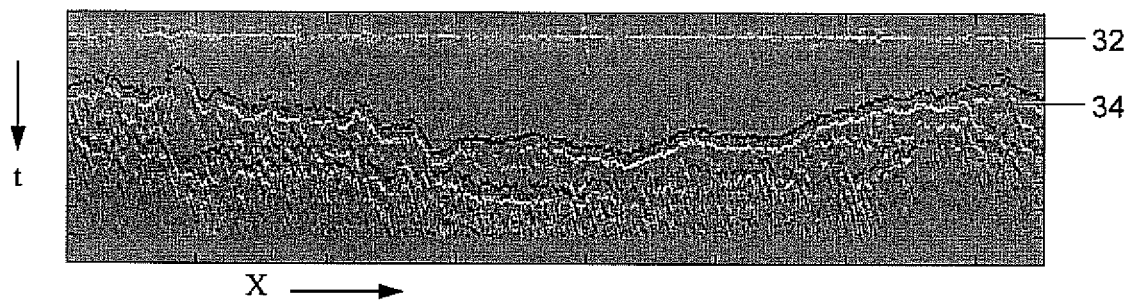

FIG. 3c a shows ToFD image based on the data signals used for obtaining the ToFD image according to FIG. 3b after being processed by a second and third substep;

FIG. 3d shows a ToFD image based on data signals used for obtaining a ToFD image according to FIG. 3c after being processed by a fourth substep;

FIG. 3e shows a ToFD image based on data signals used for obtaining the ToFD image according to FIG. 3d after being processed by a processing step d.;

FIG. 3f shows a ToFD image based on data signals used for obtaining the ToFD image according to FIG. 3e after being processed by a processing step c.;

FIG. 4a schematically shows how the set of data signals for obtaining the ToFD image according to FIG. 3a is obtained;

FIG. 4b shows schematically how the set of data signals is obtained after being processed according to the first substep;

FIG. 4c shows the same as FIG. 4b;

FIG. 4d shows schematically how the set of data signals is obtained after being processed according to the second substep;

FIG. 5a shows how a data signal is obtained if a pulse is reflected on a defect;

FIG. 5b shows how a data signal is processed by means of a Sparse Spike Deconvolution;

FIG. 6 shows schematically the processing of a data signal according to processing step d.;

FIG. 7 shows a method for carrying out the processing step d. according to FIG. 6;

FIG. 8a shows an example of a ToFD image obtained on the basis of data signals which data signals are not processed according to a method according to the invention; and FIG. 8b shows a ToFD image obtained on data signals after having been processed by a method according to the invention.

Figure 2A:
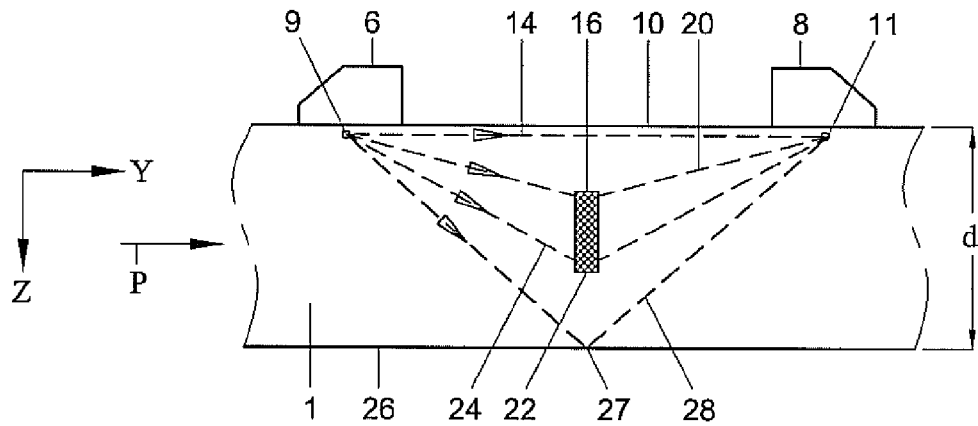
FIG. 2a shows a system for carrying out a method according to the invention.

FIG. 2a shows a system for carrying out a method for inspecting an object 1 by means of ultrasound. The method is for example for detecting a wall thickness D of the object 1 or for detecting defects 2 in the object.

For carrying out a method according to the invention, in a step a. at least one ultrasonic pulse is transmitted into the object 1 by means of a transmitter 6. In this example the frequency of the ultrasonic pulse is at least 100 kHz. The transmitted pulse travels towards a receiver 8. The transmitter 6 is situated on a first position 9 on a surface 10 of the object 1 whereas the receiver 8 is located on a second position 11 on the surface of the object. This is a first pair if a first location and a second location to be used for a measurement.

For example at t=t0 an ultrasonic pulse 12 is transmitted by means of the transmitter 6 into the object 1 on the first position 9. In FIG. 2c this ultrasonic pulse is indicated with reference number 12. The ultrasonic pulse 12 propagates directly towards the second position 11 along the surface 10 of the object 1. This is called the lateral wave 14. This lateral wave 14 is received on the second position by means of the receiver 8 on the moment in time t=t1 (see FIG. 2c).

Furthermore, the transmitted pulse also travels towards the end portion 16 of a defect 2 (see FIG. 2a). The ultrasonic pulse 12 is diffracted on this end portion 16 amongst others in a direction of the second position 11 and is received in the receiver 8 on the moment in time t=t2. The path along which the pulse travels when it is received at the moment in time t=t2, is indicated with reference number 20. Similarly, the pulse is also diffracted on a second end portion 22 of the defect 2. This diffraction results in the pulse also being received at the moment in time t=t3. The path along which the pulse travels to be received on the moment in time t=t3, has been indicated with reference number 24.

Finally, the pulse is also received on the moment in time t=t4 due to a reflection of the pulse on portion 27 of a lower surface 26 of the object. The path along which the pulse travels when it is received at the moment in time t=t4, is indicated with reference number 28. As shown in FIG. 2c, the transmitted pulse is thus received on different moments in time, in this example on the moments in time t1, t2, t3 and t4 respectively. It is noted that t2 represents a distance between the position of portion 16 and the surface 10, t3 represents a distance between the position of portion 22 and the surface 10, t4 represents a distance between the position of portion 27 and the surface and t1 represents a distance between the first position 9 and the second position 11. The relation between the value of ti (i=1, 2, 3, or 4) with the associated distance is of a non-linear nature.

Figure 2B:
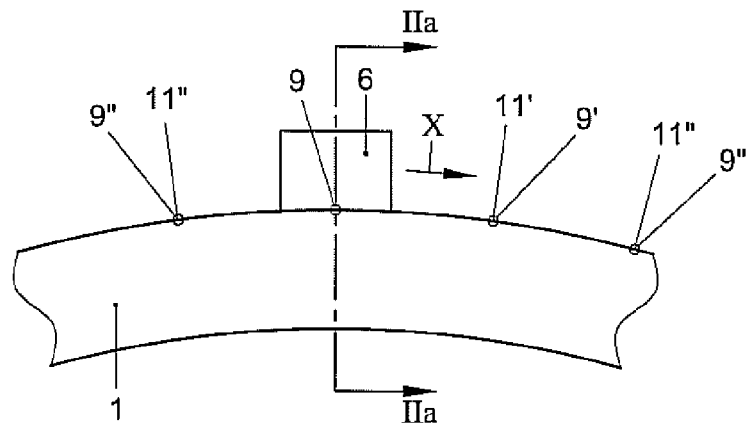
Figure 2C:
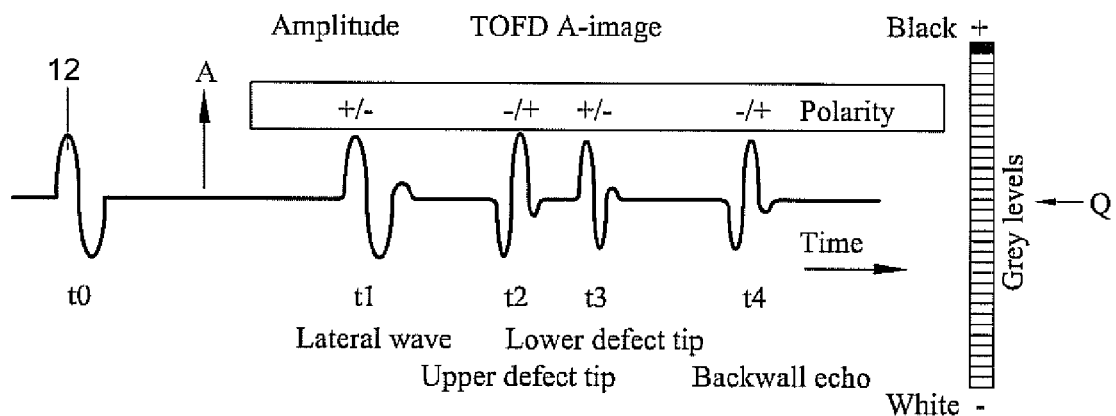

After that a data signal according to FIG. 2c is generated, the transmitter 6 and the receiver 8 are both shifted in a direction x as shown in FIG. 2b. In this example, the transmitter 6 is relocated at a new first position 9'. Also the receiver 8 is relocated towards a new second position over a same distance as the transmitter 6. Thus a new pair of a first location and a second location is used for a next measurement. Then a new ultrasonic pulse 12 is transmitted and received in a same manner as shown in FIG. 2c. Thus a second data signal according to FIG. 2c is obtained. Subsequently, a next data signal according to FIG. 2c is obtained by moving the transmitter and the receiver further in a direction x towards a new first position 9" and a new second position 11" respectively. Thus in this way a first set of data signals is obtained. (The distance between the receiver and the transmitter remains the same in this example. Lines which interconnect the first and second position for successive shifts are parallel to each other because they are shifted in the direction x, also referred to as scanning direction. If the body is a weld of a pipeline the direction x usually extends in a radial direction of the weld. If the body is a flat plate the direction x usually extends in a longitudinal or transverse direction of the plate. As becomes clear from FIG. 2b the body 1 is curved and may for example be formed by a pipeline or a weld of a pipeline.) As can be seen in FIG. 2c, based on the amplitude A of a received pulse, a grey scale can be defined. If the amplitude is zero, this corresponds with a predetermined grey colour Q. If the amplitude becomes higher, this corresponds with a darker colour than the predetermined grey colour belonging to amplitude zero. If the amplitude is negative, the corresponding colour is less grey than the predetermined grey colour. If the amplitude is more negative, the corresponding colour is even less grey towards white.

FIG. 3a shows a way in which the first set of data signals can be represented in a ToFD image. The horizontal direction corresponds with the direction x indicating the subsequent positions 9,11 where a pulse is transmitted and received and thereby indicating a specific data signal belonging to these positions. This direction is also referred to as a scanning direction. The vertical direction corresponds with the moment in time whereon a pulse is received. As explained above, this moment in time corresponds with a distance to the surface 10. The colour represents the amplitude of a signal (the amplitude of a received pulse) Hence, based on a position of a pattern of colours in the direction of axes t in FIG. 3a, the moment in time on which a pulse is received can be determined. Based on the position of a pattern of colours in the direction x it can be seen at which position the defects are located along the scanning direction. The amplitude of the data signal can be determined on the bases of the colour in FIG. 3a.

In FIG. 3a the top line 30 corresponds to the receiving of the pulse as a lateral wave 14. The line 32 corresponds to pulses which have travelled along the path 28 (pulses with have reflected on the wall 27). The arc 36 may be caused by a defect 2. The arc 36 may be caused by a pore (a defect with no length in the scanning direction x). A defect having a length perpendicular to the surface 10, such as shown for the defect 2 in FIG. 2a, will result in two pulses being received at different moments in time. The time difference t3-t2 is a measure for the length of the defect in the direction Z (see FIG. 2a). A pore having no length in the scanning direction X also results in an arc 34 in the ToFD image according to FIG. 3a. This is based on the fact that is detected on the basis of the receiver and the transmitter being on different pairs of locations 9,11 respectively due to shifting of the locations 9,11 in the direction X, so that these different pairs of locations result in different travel times for the pulses being received.

For example, if the transmitter and the receiver are on the first and second location 9', 11' respectively, t2 and t3 may (belonging to the defect 2) increase relative to t2 and t3 for the measurement when the transmitter and the receiver are on the first and second position 9,11 respectively. Also t2 and t3 may increase if the transmitter and the receiver are relocated on a position 9''', 11''' respectively. Thus assuming that the defect is in FIG. 2b just below the positions 9, 11 respectively, t2 and t3 will be minimal on this position. For all other positions t2 and t3, t3 will increase resulting in an arc 36 in the ToFD image.

If the defect has a certain length in the direction Z and does not have a length in the direction X (a pore), t2 and t3 will not be the same. The result will be two arcs 34 in the ToFD image. If the defect does not have a length in the direction Z but will have a length in the direction X then t2 and t3 will be the same but the result will again be an arc 36. As can be seen in FIG. 3a, the arc 36 consists of a white line and a black line indicating that a pulse is received on one moment in time whereas for the arc 34 it holds that a white line and a black line as well as a black line and a white line are shown, indicating that the pulse is received on different moments in time t2 and t3 respectively.

According to an example of the present invention, the first set of data signals which are used for generating the ToFD image of FIG. 3a will be processed in several steps for improving the ToFD image.

First the first set of data signals are processed according to step b. Step b. comprises in this example a first substep, a second substep and a third substep. The first substep processes each of the individual data signals of the first set of data signals. The first substep comprising correcting each data signal for a NMO (Normal Move Out) which correcting simulates a measurement wherein the corrected data signal would correspond to a data signal obtained if the first position and the second position would coincide. FIG. 3b shows a ToFD image which would be obtained on the basis of the data signals which each have been corrected by means of the first substep. The result of the first substep will be explained based on FIG. 4a and FIG. 4b respectively. FIG. 4a corresponds with FIG. 2. These figures for clarity reasons do not show the transmitter and the receiver, however they are positioned on the first and second location 9, 11 respectively.

The first substep simulates a measurement with a transmitter and a receiver at the same position 9, 11 (for example at a weld centre line as shown in FIG. 4b). This first substep (NMO) must be carried for each data signal separately. As shown in FIG. 4b after correction of the data signals, the data signals are such that the pulses are received on moments in time which would correspond with the situation wherein the first location 9 of the transmitter and the second location 11 of the receiver are on the same position as shown in FIG. 4b. This implies in this example corrected values for t2 (because the length of a1+a2 in FIG. 4a is shorter than twice the length of a3 in FIG. 4b), corrected values for t3 (because the length of b1+b2 in FIG. 4a is shorter than twice the length of b3 in FIG. 4b) and corrected values for t4 (because the length of c1+c2 in FIG. 4a is shorter than twice the length of c3 in FIG. 4b). In this example after correction it holds for the lateral wave that t0=t1 because position 9 and position 11 are simulated to coincide.

The data signals which are obtained after being corrected by means of the first substep are then processed according to a second substep. The second substep comprises correcting a data signal for the propagation velocity of the ultrasound in the object which correction simulates a measurement wherein the propagation velocity is half the value of the real propagation velocity, such that the corrected data signal simulates a single physical measurement wherein all secondary sources indicated as (16,9), (16,22) and (16,27) fire (reflecting and/or diffracting the transmitted pulse) simultaneously form the actual position where such reflection and/or diffraction occur. This is shown in FIG. 4d. The second substep is carried out for enabling the possibility to carry the to be discussed third substep. The object of this second substep is to simulate the data signals in such a way that the individual data signals (ToFD measurements) simulate a single physical measurement. This can be understood by comparing FIG. 4c with FIG. 4d. In FIG. 4c (which corresponds to FIG. 4b.) a pulse is transmitted from the first location 9, travels to an end portion 16 of a defect 2 and then (due to diffraction) travels back to the first location 9 which coincides with the second location 11 for receiving the diffracted pulse (echo signal). After having applied the second step, the data signals are corrected in such a way that it is simulated that the pulse (echo signal) which is received on the second location 11 is generated by a transmitter which is located at the end portion 16 (in FIG. 4d indicated as the secondary source (16,9)). Because in that simulation the distance to be travelled by the echo pulse is half of the distance along which the echo pulse has to travel in FIG. 4c the correction is a simulation of a measurement wherein the propagation velocity is half the value of the real propagation velocity. The same applies to the pulse which is diffracted on the second end portion 22. After having carried out the second substep to this data signal, the data signal simulates the situation wherein the received pulse is transmitted from the location (22,9) corresponding to the position of the second end portion 22. In FIG. 4c the transmitted pulse is also reflected on the position 27 and after applying the second substep, the data signal simulates as if the transmitter is present at the location (9, 27) as shown in FIG. 4d. Due to the second substep it is also simulated that the secondary sources (16,9), (22,9) and (27,9) transmit (fire) simultaneously. After having carried out the second step it also simulated that the transmitter at the location indicated with (11,9) in FIG. 4d. transmits simultaneously with the secondary sources at the locations (16,9), (22,9) and (27,9).

After having applied the second substep to each of the data signals which are obtained by the first substep, a second set of data signals is obtained.

The third substep comprises processing the second set of data signals in combination. The third substep processes the data signals in such a way in combination so as to determine a third set of data signals according to the principal of inverse wave field extrapolation. Said third set of data signals indicate where in the interior of the object the reflections and/or diffractions occur. Basically, the second set of data signals is back propagated to every point in the image space, through a medium with half the real wave propagation speed and only the zero time samples of the back propagated wave field is retained. If in an image point a secondary source fires at time equals zero, an image amplitude will be obtained in this way. If no secondary source was present, the resulting image amplitude will be zero.

The second set of data signals is obtained by receiving signals which are distributed in one dimension over the surface of the object. In this example, this one dimension is the direction x along which the transmitter and the receiver are replaced for obtaining the subsequent data signals. The data signals of the second set are processed in combination. On the basis of these data signals, using inverse wave field extrapolation, the detected wave field can be traced back to the position where it came from, particularly the position of virtual sources (16, 22, 27) that arise due to reflections and/or diffractions of the ultrasound supplied to the material of the object. In case of an examination of a weld of a pipeline, a virtual sources may correspond to the position of a welding defect. The data signals of the second substep are the starting point of the inverse wave field extrapolation. On the basis of the data signals, the time can be mathematically inverted. With the inverse wave theory, the detected wave field strays back to the position where it came from, namely the position of the virtual sources (16, 22, 27). The wave theory takes into account both the amplitude and the delay of the signal. The process of tracing back the wave field measured is called the inverse wave field extrapolation. The result gives the two-dimensional positions, shape and magnitude of the virtual sources, which each shape magnitude and position of a virtual source in fact being determined by the position of a collection of point sources on which the virtual sources is made. Because according to the invention, the data signals are processed which come from ultrasonic receivers distributed in one dimension over the surface of the object, a resolution is obtained which is more or less equal in all directions. In addition, thus an actual two dimensional image of the material of the object can be obtained. Based on the data signals which are obtained after carrying our a third substep a ToFD image is generated. Such ToFD image is shown in FIG. 3c. FIG. 3c shows that the arcs 36 of FIG. 3a have collapsed. What remains are the arcs 34 which are however true defects having a certain length. Because the arcs 36 have been collapsed into a dot, in FIG. 3c it is clear that the resolution of the image in a direction x is improved. The arc 36 in FIG. 3a corresponds with a defect having no length in the direction z and it is clear that the resolution in the direction t of FIG. 3c has significantly improved because the defect 36 which has no length in the direction y is now in the form of a dot.

After having carried out the third substep in step b. a further fourth substep is carried out on out of the data signals obtained in the thirds substep. Thus, the third set of data signals which is obtained in the third substep is processed in the fourth substep wherein the fourth substep is the inverse of the first substep so that the third set of data signals is transformed back to signals representing the true first position of the transmitter and true second position of the receiver. The data signals which are obtained after carrying out the first substep can also provide a basis for generating a ToFD image. Such ToFD image is shown in FIG. 3d. A difference with the ToFD image according to FIG. 3c is that in FIG. 3d the axis in the direction t is non-lineair again (the same as in FIG. 3a). This is because after applying the fourth substep the position 9 and the position 11 no longer coincide. This results in that t2 and t3 do not have a linear relation with the distance between the end portion 16 and the surface 10 and the distance between the end portion 22 and the surface 10.

Please note that it is not necessary to carry out the fourth substep. It is also noted that it is possible that the first substep and the second substep are carried out in a reversed order. Hence, it is possible that after that first the second substep is carried out subsequently the first substep is carried out based on data signals obtained by means of the second substep. The second substep is then carried out based on the data signals belonging to the first set of data signals. The data signals which are obtained by the first substep are further processed by means of the third substep as discussed above.

In this example the data signals which are obtained by means of the fourth substep are further processed in a step d. According to step d. in each data signal obtained by the fourth substep the phase of the transmitted pulse is removed wherein this phase comprises the phase spectrum preferably in combination with the amplitude spectrum of the transmitted pulse. Thus the processing of the first set of data signals in this example comprises a step d. wherein in step d. in each data signal the phase of the transmitted pulse is removed. This is called zero-phasing. The object of this step is to remove the source signature phase (note: the phase is defined here as the phase spectrum used in combination with the amplitude spectrum to mathematically describe a signal) from the measured ToFD signal. The advantage of doing this lies in the fact that the highest amplitude in the reflected signal will be observed at the 'event time' $t_e$ (the event time is the real time of flight from transmitter, to defect (t2-t0, t3-t0) or reflecting surface (t4-t0), to receiver, this is also referred to as onset). The effect of zero-phasing is shown in FIG. 6.

An overview of the signal processing for zero-phasing is shown in FIG. 7. A critical aspect of zero-phasing is finding the original source wavelet phase information. Although this can be done in different ways, in this case the source wavelet phase is extracted from the measurement data itself, by using the relationship between real and imaginary part of the pulse in the frequency domain, called the Kramers-Kronig relationship. This is an elegant and efficient approach, as no additional measurements or probe data sheets are required and it can be done offline. In FIG. 7, the operations inside the block 48 are the operations performed to obtain the phase information of the source wavelet.

In FIG. 7 the following is shown. In block 40 a received data signal is shown. This data signal is transformed to the frequency domain in block 42. This leads to the data signal s(t) (as shown in FIG. 2c) being transformed to its counterpart S(f). S(f) can be written as:

$$S(f) = |S| \cdot e^{-i\phi_s} \quad \text{Equ 1}$$

Equation 1 can also be written as $$S(f) = |D| \cdot |W| \cdot e^{-i(\phi_1 + \phi_w)} \quad \text{Equ 2}$$

Where $|D|$ is the amplitude spectrum of a series of spikes relating to defects, $|W|$ is the amplitude spectrum of the source wavelet, $\phi_D$ is the phase information of the series of spikes related to the defects and $\phi_W$ is the phase information. From $$\ln|S| = \ln|D| + \ln|W| \quad \text{Equ 3}$$

the source amplitude spectrum $|W|$ can be found by applying a smoothing filter (or cepstrum technique) to ln $|S|$, in order to eliminate ln $|D|$, which is supposed to vary rapidly in the spectrum. Once $|W|$ has been found, and assuming that the signal is causal (which applies to all probe pulses), the KramersKronig relationship can be applied to find the source phase information $\phi_W$ from the source amplitude spectrum $|W|$. The KramersKronig relationship is solely based on causality and implies no further assumption other than the causal behavior of the processed signal. Once $\phi_W$ has been obtained, it can be subtracted from the $\phi_S$, leaving only the defect phase information in the zero-phased signal $S_{ZP}$ (f):

$$S_{zp}(f) = |D| \cdot |W| \cdot e^{-i\phi_D} \quad \text{Equ 4}$$

Transforming $S_{ZP}$ (f) back to the time domain gives the zero-phased measured time signal $S_{ZP}$ (t), as shown in FIG. 7. In block 44 it is shown that it holds for the amplitude spectrum that $|S| = |D||W|$. This corresponds with equation 3. In block 46 it is indicated that it holds for the phase spectrum $\phi s = \phi d + \phi W$.

In block 48 the determination of (W) (using smoothing cepstrum) is indicated followed by the Kronig relationship. This results in $\phi w$ in block 50. In block 52 based on block 46 and block 50, $\phi d$ is obtained. The result of this is shown in block 54. Based on block 54 and block 44 the zero-phased signal in the frequency domain is obtained. This is shown in block 56. By transforming the zero-phased signal in the frequency domain back in block 58 to the time domain the zero-phased signal in time is obtained in block 60.

If based on the thus obtained data signals a ToFD image is obtained such ToFD image is shown in FIG. 3e. Zero-phasing according to step d. is in fact transforming the input pulse to a symmetric shape wherein the maximum amplitude occurs at the true trigger moment of the pulse. Of course the result is no longer a causal pulse. This is not a problem because it is used only in a computer as a means for accurate and unambiguous measurement of pulse timing. In this respect it is noted that a computer is used for each of the steps carried out for processing the data signals.

It is noted that step d. can also be carried out before step b. is carried out. Step d. can also be carried out between any of the substeps of step b. It can also be carried out after that step b. is carried out. However, in case the still to be discussed step c. is carried out step d. should always be carried out before step c. is carried out.

In the present example, after having carried out step d. a final step c. is carried out.

Step c. comprises processing each data signal (in this example data signal obtained after having carried out step d.) wherein each pulse in a data signal is replaced by a spike, preferably by means of a Sparse Spike Deconvolution. Other methods than deconvoluting methods are also possible. Step c. aims at removing the pulse shape from the image all together. Anywhere where the process recognizes a pulse it replaces it with a spike. The process will only work if one knows beforehand that relatively few defects are present on any given data signal. FIG. 5a shows how the actual signal 61 consists of a spikey indication 62 (a receiving of a transmitted pulse by means of a lateral wave, by means of a reflection and/or by means of a diffraction) convolved with the source pulse 64 as transmitted. The deconvolution process applies the inverse pulse shape 66 of the transmitted pulse 64 to the data signal 61 as received to obtain a data signal 68 comprising spikey indications 62 (FIG. 5b).

The deconvolution process itself is carried out by deconvoluting the data signal with a predetermined pulse which corresponds with the transmitted pulses. This predetermined pulse may be determined on the basis of at least one received data signal. For stabilisation of the deconvolution algorithm the sparseness assumption may be relevant. This is referred to as the Sparse Spike Deconvolution. This means that it is assumed that in the data signals only a limited amount of diffraction and reflections (events) occur.

The Sparse Spike Deconvolution is thus to remove the source signature 64 (the predetermined pulse) from the data signals 61, leaving only spikes 62 in the data signal 68 at the times that events occurred. The advantage of having spikes instead of wavelets is the increased resolution and ease with which defects can be located in a ToFD image.

The background behind this is to consider the signal as an assumption of events (spikes) 62 that are convoluted with the source signature:

$$\Delta(t) = \sum_i n_i \cdot \omega(t - t_i) \quad \text{Equ. 5}$$

where $t_i = i\, \delta t$ and $\delta t$ is the sampling interval. Thus the sampling interval equals the pulse repetition frequency wherein pulses are transmitted.

The summation of equation 5 can also be written as a multiplication of vectors and matrices:

$$\underline{\Delta} = \underline{W} \cdot \underline{n} \quad \text{Equ. 6,}$$

where W is a Toeplitz matrix. From this, the function r describing the events can be found by using for example at least square inversion, $$\underline{n} = \frac{\underline{\underline{W}}^T \cdot \underline{\Delta}}{\underline{\underline{W}}^T \cdot \underline{\underline{W}} + \varepsilon \underline{\underline{I}}} \qquad \text{Equ. 7}$$

but other techniques can be applied as well. In equation 7 T indicates the transposed of a matrix and epsilon is a small stabilising constant, while I stands for the identity matrix.

The nature of ToFD data is such that only a limited number of detect events is expected per signal. This feature allows the invocation of an error that should be minimized in order to find the function r, which favours sparse solutions. This error norm F can be written as the sum of a regular least squares error norm and a sparseness enhancing additive or multiplicative function:

$$F_{sparsen} = \left\| \Delta_{(t)} - \sum_i n_i \cdot w_{(t-t_i)} \right\|^2 + F_{cauchy}(\underline{n}) \qquad \text{Equ. 8}$$

where FCauchy is the Cauchy distribution function, which forces sparseness in the solution. It should be noted that sparseness can also be introduced by other distributions than the Cauchy (e.g. an L1 norm etc.), but the Cauchy norm works very well.

The function r represents the data signal 68 comprising the spikes 62 wherein the function may represent the source signature (predetermined transmitted pulse 64 used for replacing a pulse in the data signal by a spike). Based on equation 8 the function r can be determined and thereby the signal 68 as shown in FIG. 5*b* is determined. In this example the sparse spike deconvolution is carried for the data signals based wherein image 4*c* is obtained. Based on the thus obtained data signals, a ToFD image is obtained as shown in FIG. 3*f*. As shown in FIGS. 3*e* and 3*f* the line 30 is now in the top of the image. This is a result of the zero-phasing image wherein the top of the image corresponds with the moment on which the lateral waves arrive at the second location. It is clear that the ToFD image of FIG. 3*f* is more easy to evaluate because disturbing influences (pulse length, hyperbolic shape, noise, interference) have been significantly reduce or even removed. As shown in FIG. 3*f*, the arcs 34 now do have a very high resolution as well as the line 32. The line 30 is now on the top of the image which is a result of the zero-phasing as supplied in step d.

Figure 1A:
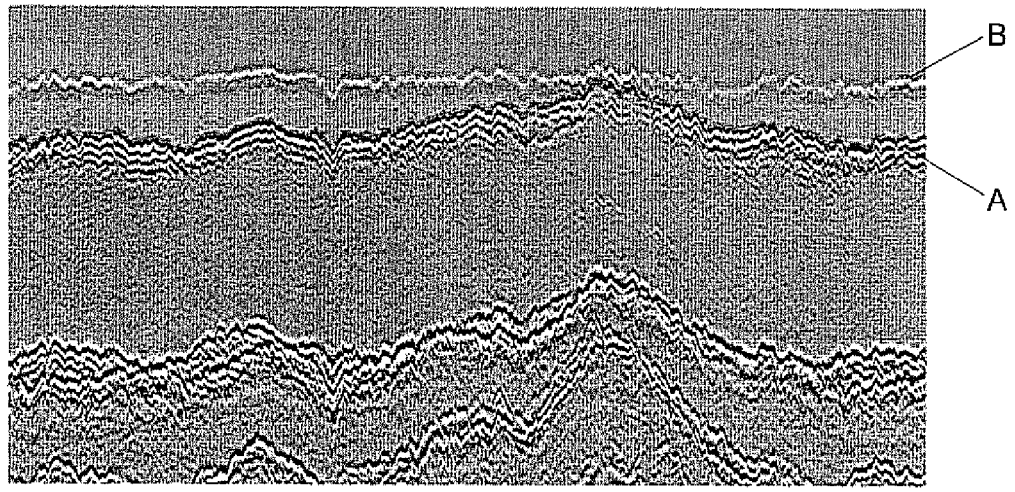
FIG. 1a shows a ToFD image obtained by a known method.
Figure 2D:
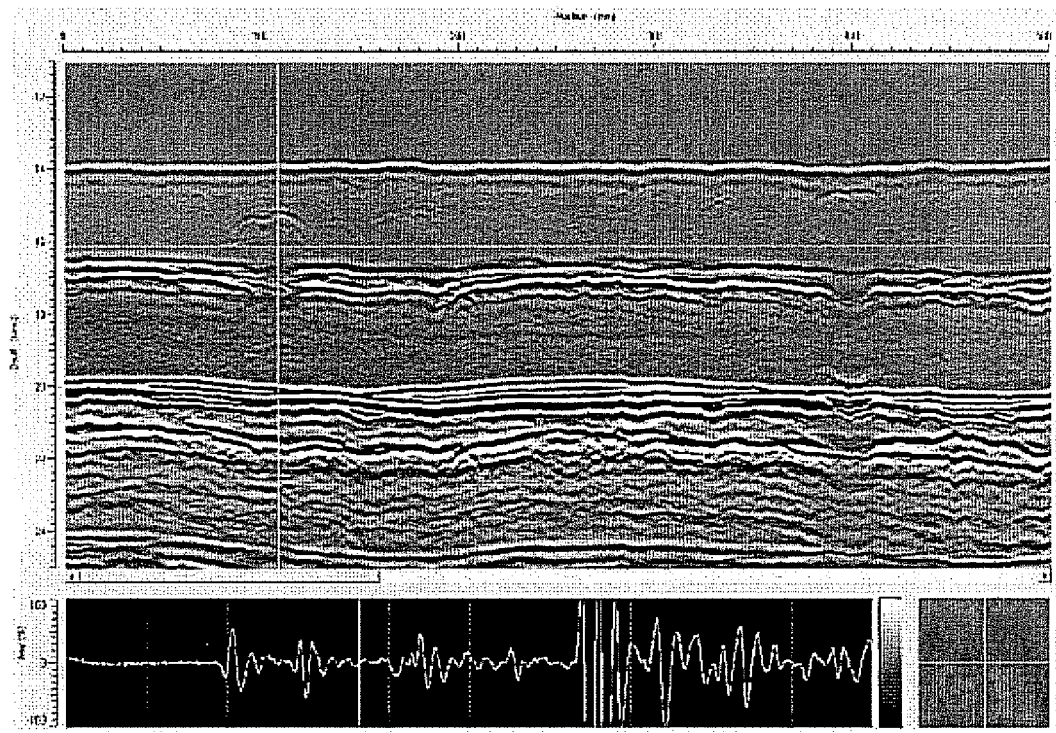
FIG. 2d shows a ToFD image obtained on the basis of data signals according to FIG. 2c.
Figure 1B:
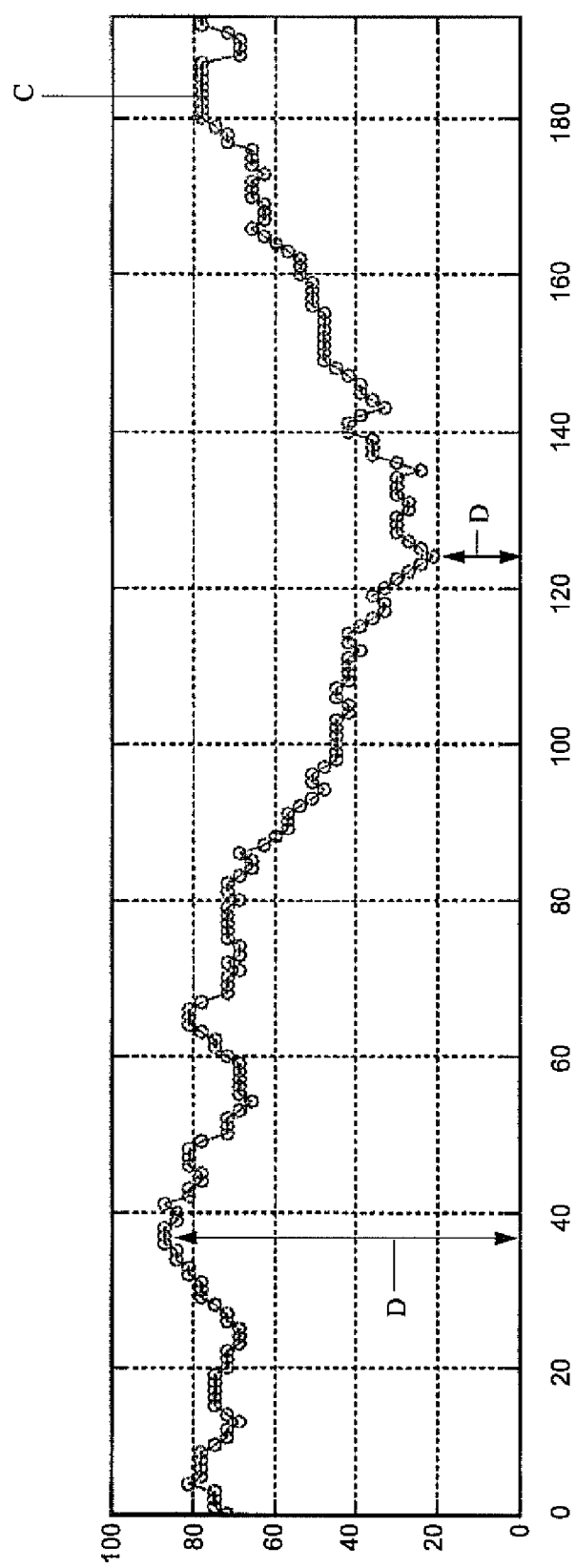

In the above example, it has been demonstrated how data processing rather then image processing can be used to remove inherent features of the measurement from the data signals. This same process including each of the steps as discussed above, will now be applied to a root corrosion example similar to the one used in FIG. 1*a* and FIG. 1*b*. In FIG. 8*a* the original data are shown as a result of a weld scan. Thus FIG. 8*a* shows a ToFD image based on data signals received at the second locations. These received data signals are directly used for generating the ToFD image of FIG. 8*a*. Next to these data signals all data processing steps as discussed above (step b. comprising the first substep, the second substep, the third substep and the fourth substep, step d. and step c. respectively) are carried out. The result is shown in the ToFD image according to FIG. 8*b*. It can be seen that both the lateral wave 32 and the profile of the back wall 34 have been reduced to a thin line. This is a good illustration how the near-surface resolution and defect detection capabilities are improved by using these techniques. Possible small indications will have no influence on the final result. In addition, sizing result in ToFD data thus processed will be more accurate. Last but not least, interpretation will be more robust. The latter will make such processing algorithm especially fit to be used as a basis for automatic interpretation of ToFD signals. Said automatic interpretation can for example involve determining on several positions the distance between the lines 32 and 34 and thereby the wall thickness.

The invention is not limited to the above referred to special embodiments. For example, the sequence of the first substep and the second substep may be reversed. The fourth substep may be deleted. Step d. should be carried out before step c. if step c. is applied. Nevertheless step d. may be carried out between any of the steps preceding step c. Step d. may also be applied on the first data set without being combined with step c. and/or step b. If only a wall thickness has to be obtained, only step c. may be applied. Such variations all fall within the scope of the invention. The improved processing for ToFD signals can be used for scanning all kind of bodies such as metal bodies, plastic bodies and bodies from other materials, including plates, pipelines, and welds. It may be used for detecting defects in such bodies and/or determining wall thicknesses from such bodies.

The invention claimed is:

1. A method for inspecting an object by means of ultrasound for detecting a wall thickness of the object or for detecting defects in the object, wherein in a step a. at least one ultrasonic pulse is transmitted by a transmitter into the object on a first position of a surface of the object, the ultrasonic pulse is received by a receiver on a second position of the surface of the object by propagating directly towards the second position along the surface of the object or as a result of reflection and/or diffractions of the pulse in the object so that the transmitted pulse may result in more than one pulse being received by the receiver at different moments in time and wherein a data signal is generated representing the received pulses and the associated moments in time wherein these pulses are received wherein step a. is repeated for other first positions and/or second positions for generating a first set of data signals and wherein the first set of data signals obtained in the plurality of steps a. are processed for generating processed signals on the basis of which a ToFD (time of flight diffraction) image can be obtained, wherein the ToFD image indicates a wall thickness or defect of the object, characterized in that the processing for obtaining the processed data signals comprises a processing step b. and a processing step c. performed by at least on computer central processing unit, wherein:

the step b. comprises a first substep, a second substep and a third substep wherein the third substep is applied to a second set of data signals wherein the second set of data signals are obtained by processing each data signal of the first set of data signals wherein for obtaining the second set of data signals each data signal of the first set of data signals is first processed in the first substep wherein each signal which is processed in the first substep is subsequently processed in the second substep or wherein for obtaining the second set of data signals each data signal of the first set of data signals is first processed in the second substep wherein each data signal which is processed in the second substep is subsequently processed in the first substep wherein:

the first substep comprises correcting a data signal for a NMO (Normal Move Out) which correction simulates a measurement wherein the corrected data signal correspond to a data signal which would have been obtained if the first position and the second position would coincide; the second substep comprises correcting a data signal for the propagation velocity of the ultra sound in the object which correction simulates a measurement wherein the propagation velocity is half the value of the real propagation velocity such that the corrected data signal simulates a single physical measurement wherein all secondary sources for reflecting and/or diffracting the transmitted electronic pulse fire simultaneously; and the third substep comprises processing the second set of data signals in combination in order to determine a third set of data signals, according to the principle of inverse wave field extrapolation, which third set of data signals indicate where in the interior of the object the reflections and/or diffraction occur;

wherein step c. comprises processing each data signal, wherein each pulse in a data signal is replaced by a spike indicating a wall thickness or defect of the object.

2. The method according to claim 1, characterized in that for determining defects in the object at least step b. is carried out.

3. The method according to claim 1, characterized in that, the ToFD image is automatically evaluated to determine defects in the body and/or a thickness of a wall of the body.

4. The method according to claim 1, characterized in that step b. further comprises a fourth substep wherein each data signal of the third set of data signals is processed in the fourth substep wherein the fourth substep is the inverse of the first substep so that the third set of data signals is transformed back to signals representing the true first position and true second position.

5. The method according to claim 1, wherein, in step c. each pulse in a data signal is replaced by a Deconvolution process.

6. A method for inspecting an object by means of ultrasound for detecting a wall thickness of the object or for detecting defects in the object, wherein in a step a. at least one ultrasonic pulse is transmitted by a transmitter into the object on a first position of a surface of the object, the ultrasonic pulse is received by a receiver on a second position of the surface of the object by propagating directly towards the second position along the surface of the object or as a result of reflection and/or diffractions of the pulse in the object so that the transmitted pulse may result in more than one pulse being received by the receiver at different moments in time and wherein a data signal is generated representing the received pulses and the associated moments in time wherein these pulses are received wherein step a. is repeated for other first positions and/or second positions for generating a first set of data signals and wherein the first set of data signals obtained in the plurality of steps a. are processed for generating processed signals on the basis of which a ToFD (time of flight diffraction) image can be obtained, wherein the ToFD image indicates a wall thickness or defect of the object, characterized in that the processing for obtaining the processed data signals comprises a processing step b., and at least one processing step selected from a processing step c. and a processing step d. performed by at least on computer central processing unit, wherein:

the step b. comprises a first substep, a second substep and a third substep wherein the third substep is applied to a second set of data signals wherein the second set of data signals are obtained by processing each data signal of the first set of data signals wherein for obtaining the second set of data signals each data signal of the first set of data signals is first processed in the first substep wherein each signal which is processed in the first substep is subsequently processed in the second substep or wherein for obtaining the second set of data signals each data signal of the first set of data signals is first processed in the second substep wherein each data signal which is processed in the second substep is subsequently processed in the first substep wherein:

the first substep comprises correcting a data signal for a NMO (Normal Move Out) which correction simulates a measurement wherein the corrected data signal correspond to a data signal which would have been obtained if the first position and the second position would coincide;

the second substep comprises correcting a data signal for the propagation velocity of the ultra sound in the object which correction simulates a measurement wherein the propagation velocity is half the value of the real propagation velocity such that the corrected data signal simulates a single physical measurement wherein all secondary sources for reflecting and/or diffracting the transmitted electronic pulse fire simultaneously; and the third substep comprises processing the second set of data signals in combination in order to determine a third set of data signals, according to the principle of inverse wave field extrapolation, which third set of data signals indicate where in the interior of the object the reflections and/or diffraction occur;

wherein step c. comprises processing each data signal, wherein each pulse in a data signal is replaced by a spike indicating a wall thickness or defect of the object;

step d. comprises processing each data signal by means of zero-phasing wherein in each data signal the phase of the transmitted pulse is removed wherein this phase comprises at least the phase spectrum of the transmitted pulse.

7. The method according to claim 6, characterized in that in step d. in each data signal the phase of the transmitted pulse is removed wherein this phase comprises the phase spectrum in combination with the amplitude spectrum of the transmitted pulse.

8. The method according to claim 6, characterized in that for determining a wall thickness at least one of step d. and step c. is carried out.

9. The method according to claim 8, characterized in that step c. is carried out on the basis of signals which have been processed in step d.

10. The method according to claim 6, characterized in that step d. or step c. is carried out on the basis of data signals which have been processed in step b.

11. The method according to claim 10, characterized in that step c. is carried out on the basis of data signals which have been processed first in step b. and subsequently in step d. or on the basis of data signals which have first been processed in step d. and subsequently in step b or on the basis of data signals which have been processed in step b wherein step d is carried out between two of the substeps of step b.

12. The method according to claim 6, characterized in that step c. and step d. are combined into one step.

13. The method according to claim 6, characterized in that step c. comprises a deconvolution of a data signal based on a predetermined transmitted pulse.

14. The method according to claim 13, characterized in that step c. comprises applying the inverse shape of the predetermined transmitted pulse on the data signal for converting pulses in the data signal into spikes by deconvoluting data signal with a predetermined pulse which corresponds with the transmitted pulses.

15. The method according to claim 13, characterized in that the predetermined transmitted pulse is obtained from at least one of the data signals.

16. The method according to claim 6, characterized in that in step d. in a data signal first information is obtained about the original source wavelet phase wherein this information is subsequently used for removing this original source wavelet phase from the data signal.

17. The method according to claim 14, characterized in that the predetermined transmitted pulse is obtained from at least one of the data signals.

18. A method for inspecting an object by means of ultrasound for detecting a wall thickness of the object or for detecting defects in the object, wherein in a step a. at least one ultrasonic pulse is transmitted by a transmitter into the object on a first position of a surface of the object, the ultrasonic pulse is received by a receiver on a second position of the surface of the object by propagating directly towards the second position along the surface of the object or as a result of reflection and/or diffractions of the pulse in the object so that the transmitted pulse may result in more than one pulse being received by the receiver at different moments in time and wherein a data signal is generated representing the received pulses and the associated moments in time wherein these pulses are received wherein step a. is repeated for other first positions and/or second positions for generating a first set of data signals and wherein the first set of data signals obtained in the plurality of steps a. are processed for generating processed signals on the basis of which a ToFD (time of flight diffraction) image can be obtained, wherein the ToFD image indicates a wall thickness or defect of the object, characterized in that the processing for obtaining the processed data signals comprises a processing step b., and a processing step d. performed by at least on computer central processing unit, wherein:

the step b. comprises a first substep, a second substep and a third substep wherein the third substep is applied to a second set of data signals wherein the second set of data signals are obtained by processing each data signal of the first set of data signals wherein for obtaining the second set of data signals each data signal of the first set of data signals is first processed in the first substep wherein each signal which is processed in the first substep is subsequently processed in the second substep or wherein for obtaining the second set of data signals each data signal of the first set of data signals is first processed in the second substep wherein each data signal which is processed in the second substep is subsequently processed in the first substep wherein:

the first substep comprises correcting a data signal for a NMO (Normal Move Out) which correction simulates a measurement wherein the corrected data signal correspond to a data signal which would have been obtained if the first position and the second position would coincide;

the second substep comprises correcting a data signal for the propagation velocity of the ultra sound in the object which correction simulates a measurement wherein the propagation velocity is half the value of the real propagation velocity such that the corrected data signal simulates a single physical measurement wherein all secondary sources for reflecting and/or diffracting the transmitted electronic pulse fire simultaneously; and the third substep comprises processing the second set of data signals in combination in order to determine a third set of data signals, according to the principle of inverse wave field extrapolation, which third set of data signals indicate where in the interior of the object the reflections and/or diffraction occur;

wherein step d. comprises processing each data signal by means of zero-phasing wherein in each data signal the phase of the transmitted pulse is removed wherein this phase comprises at least the phase spectrum of the transmitted pulse.

\* \* \* \* \*